US00PP21498P2

(12) United States Plant Patent
Quinn

(10) Patent No.: US PP21,498 P2
(45) Date of Patent: Nov. 16, 2010

(54) ***PANICUM* PLANT NAMED 'HURON SOLSTICE'**

(50) Latin Name: *Panicum virgatum*
Varietal Denomination: Huron Solstice

(76) Inventor: Martin Quinn, 121 St Georges Cres., Goderich, Ontario (CA) N7A-2M1

( * ) Notice: Subject to any disclaimer, the term of this patent is extended or adjusted under 35 U.S.C. 154(b) by 126 days.

(21) Appl. No.: 12/229,263

(22) Filed: Aug. 21, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—Susan B McCormick Ewoldt

(57) ABSTRACT

The new and distinct cultivar of ornamental Switch Grass, *Panicum virgatum* 'Huron Solstice', with erect culms and becoming deep wine red early in the season and light airy flowers that persist into winter. 'Huron Solstice' is suitable as a potted plant, for multi-seasonal mass or specimen landscaping, and for cut flower arrangements.

2 Drawing Sheets

Botanical classification: *Panicum virgatum.*

Variety denomination: 'Huron Solstice'.

SUMMARY, BACKGROUND AND ORIGIN OF THE PLANT

*Panicum virgatum* 'Huron Solstice', hereinafter also referred to as 'Huron Solstice' and the new plant is a new and distinct cultivar of Switch Grass. It is the result of a cross made by Martin Quinn between *Panicum virgatum* 'Heavy Metal' (not patented) as the female parent and *Panicum virgatum* 'Rehbraun' (not patented) as the pollen parent at a nursery in Goderich, Ontario, Canada and selected for further observation in 2001. The plant has been successfully propagated by division at the same perennial plant nursery in Goderich, Ontario, Canada and found to produce identical plants that maintain the unique characteristics of the original plant. The plant is stable and reproduces true to type in successive generations of asexual reproduction.

*Panicum virgatum* 'Huron Solstice' differs from its parents as well as all other *Panicum* known to the applicant, in that the new plant has some blue green foliage like 'Heavy Metal' but develops dark purple leaves early. *Panicum* 'Huron Solstice' has fewer leaves that are redder rather than the large number of the new plant that turn dark purple. Other similar Switch Grass include *Panicum* 'Prairie Fire' U.S. Plant Pat. No. 19,367. 'Prairie Fire' is has more reddish foliage than 'Huron Solstice'.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
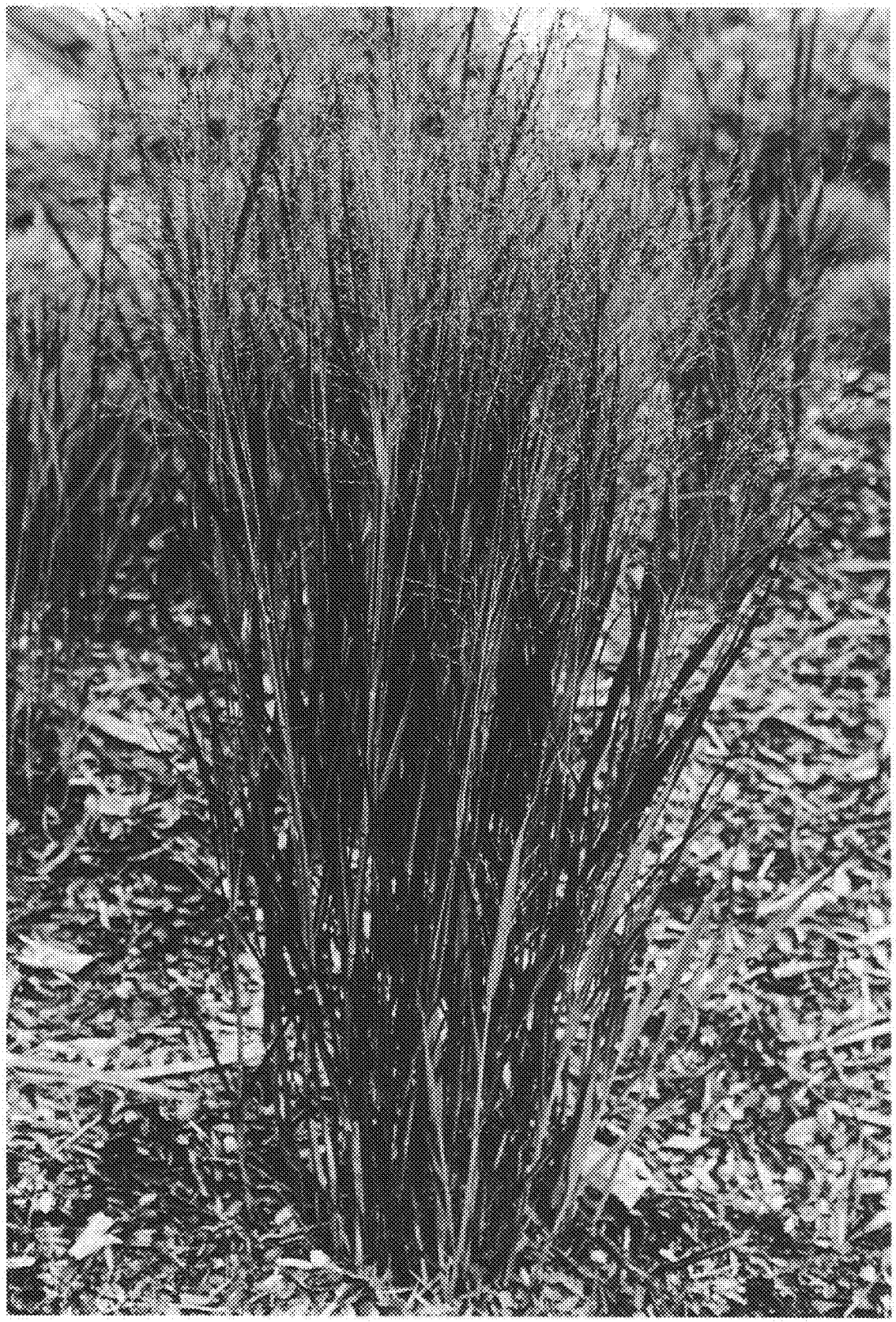
FIG. 1 shows the overall plant in mid-season.
Figure 2:
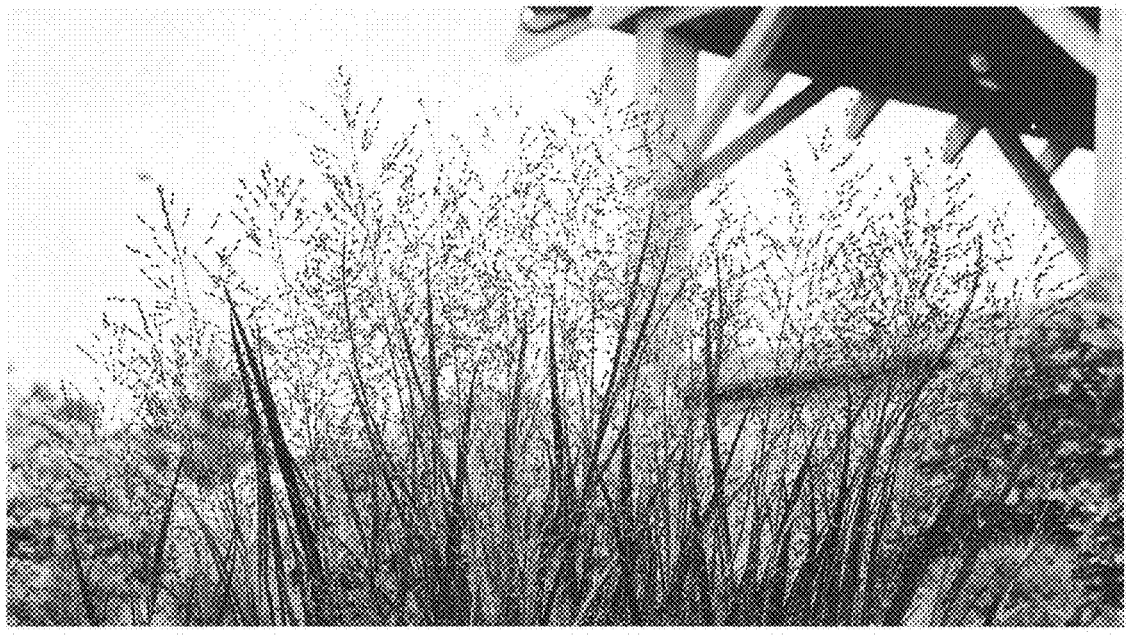
FIG. 2 shows the inflorescence in mid-July.
Figure 3:
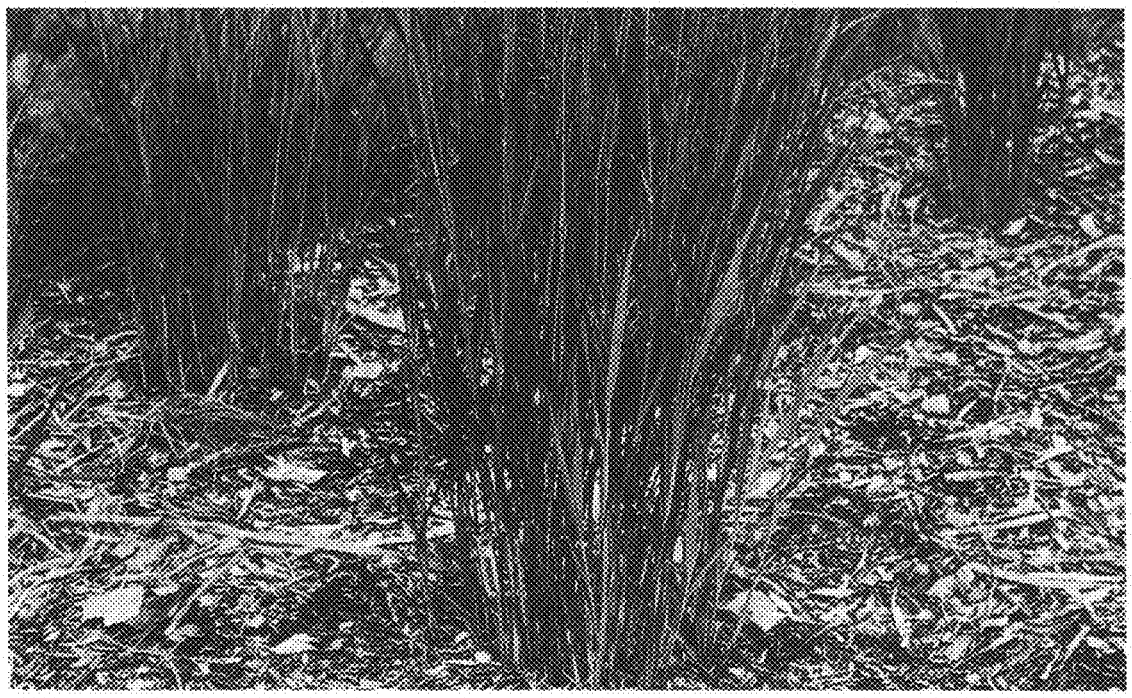
FIG. 3 shows the base of the plant with the culm habit and foliage color.

*Panicum virgatum* is native to all but the Pacific Coast states of the Mainland United States in addition to parts of Canada and Central America. There are several selected cultivars in production or commerce. *Panicum virgatum* 'Huron Solstice' differs from all of these known to the inventor in the combination of the following traits:

1. Blue green foliage that develops early in the season to a dark purple.
2. Very erect and vertical habit.

DETAILED BOTANICAL DESCRIPTION

The following descriptions and color references are based on the 2001 edition of The Royal Horticultural Society Colour Chart except where common dictionary terms are used. *Panicum* 'Huron Solstice' has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Zeeland, Mich. in full sun with supplemental water and fertilizer.

Parentage: Controlled cross of *Panicum virgatum Panicum* 'Heavy Metal'(female)×*Panicum virgatum* 'Rehbraun' (male).

Propagation method: Division of the culms.

Growth rate: Vigorous.

Time to finishing in a 3 gallon pot: Three months from liner during early summer.

Rooting habit: Normal, coarsely branching.

Plant description:

*Plant shape and habit.*—Hardy herbaceous perennial forming tightly rhizomatous clump, with erect culms topped with finely textured airy inflorescence.

*Plant size.*—Height at flowering is about 120 cm tall from ground to the top of the panicle, about 40 cm wide at ground level and 65 cm at widest point just below flowers.

Foliage description:

*Leaves.*—Glabrous, entire, flat, alternate, erect to arching toward tips, sheathed from node of attachment to ligule, linear, deciduous but persist through winter.

*Foliage size.*—About 38 cm long, about 12 mm wide.

*Foliage color.*—Adaxial side early season: RHS 133B; adaxial side mid season and later: nearest RHS 187A; abaxial side early season: closest to RHS 133B; abaxial side mid-season and later: nearest RHS N187A; some leaf areas retain the same gray green RHS 133B on both surfaces; fall color of foliage between RHS 164C and RHS 161B.

*Veins.*—Closely parallel; same color as the surrounding leaf tissue on both adaxial and abaxial sides.

*Culm.*—Glaucous, glabrous, erect, cylindrical, completely enclosed by leaf sheath, about 120 cm long including panicle about 6.0 mm wide; culm color RHS 133B.

*Flower description.*—Finely branched open panicle, one per culm, persists through winter; No fragrance detected.

*Panicle.*—Pyramidal, about 15 cm long and 15 cm wide; RHS 138B; effective August and September but persisting through winter.

*Glumes.*—Lowest outside about 3 mm long and 2 mm wide RHS 59A, inside about 4.0 mm long.

*Spikelet.*—About 5.0 mm long and 2.5 mm wide.

*Rachis.*—Variable length 2 to 5 cm, about 1.0 mm wide.

*Androecium.*—Filaments: fine, white, less than 1 mm diameter and up to 2.0 mm long; anthers: about 2.5 mm long and 1.0 mm wide, nearest RHS 31A.

*Gynoecium.*—Stigma: two, feathered, protruding 1 to 2 mm from glume, RHS 59A.

*Pollen.*—Round, less than 0.1 mm diameter, nearest RHS N 25C.

*Fruit.*—Caryopsis; 2 to 3 mm long and 1.5 mm wide, nearest RHS 164C.

Hardiness, pest and disease resistance: The plant grows best with plenty of moisture and adequate drainage, but is able to tolerate some drought once established. Hardiness at least from USDA zone 4 through 9. Disease and pest resistance or susceptibility beyond what is typical of that of other Switch Grasses has not been observed.

The invention claimed is:

1. *Panicum* 'Huron Solstice' is a new and distinct plant of ornamental Switch Grass as herein described and illustrated, with erect culms and becoming dark purple very early in the season, well suited for multi-seasonal landscape interest as a specimen or in mass, as a potted plant, and for cut flower arrangements.

* * * * *